United States Patent

Manning

[11] Patent Number: 5,914,335
[45] Date of Patent: Jun. 22, 1999

[54] PESTICIDAL 1-ARYLPYRAZOLE-5-SULFINILIMINE DERIVATIVES

[75] Inventor: David Treadway Manning, Cary, N.C.

[73] Assignee: Rhone-Poulenc Inc., Research Triangle Park, N.C.

[21] Appl. No.: 08/961,948

[22] Filed: Oct. 31, 1997

Related U.S. Application Data

[60] Provisional application No. 60/030,019, Nov. 1, 1996.
[51] Int. Cl.$^6$ .................... A01N 43/40; A01N 43/56; C07D 401/00; C07D 231/44; C07D 231/04
[52] U.S. Cl. .................... 514/341; 514/403; 514/406; 546/275.4; 546/276.1; 548/368.1; 548/372.1
[58] Field of Search ..................... 514/341, 403, 514/406; 546/275.4, 276.1; 548/368.1, 372.1

[56] References Cited

U.S. PATENT DOCUMENTS

| | | | |
|---|---|---|---|
| 4,863,937 | 9/1989 | Gehring et al. | 514/333 |
| 5,232,940 | 8/1993 | Hatton et al. | 514/407 |
| 5,236,938 | 8/1993 | Huang et al. | 514/341 |
| 5,580,843 | 12/1996 | Stetter et al. | 514/341 |

FOREIGN PATENT DOCUMENTS

| | | |
|---|---|---|
| 0301338 | 2/1989 | European Pat. Off. |
| 0385809 | 9/1990 | European Pat. Off. |
| 0403300 | 12/1990 | European Pat. Off. |
| 0659745 | 6/1995 | European Pat. Off. |
| 0679650 | 11/1995 | European Pat. Off. |
| 0295117 | 12/1998 | European Pat. Off. |
| 19511269 | 10/1995 | Germany. |
| 87/03781 | 7/1987 | WIPO. |
| 93/06089 | 4/1993 | WIPO. |
| 94/21606 | 9/1994 | WIPO. |

*Primary Examiner*—S. Mark Clardy
*Assistant Examiner*—Alton Pryor
*Attorney, Agent, or Firm*—Burns, Doane, Swecker & Mathis, L.L.P.

[57] ABSTRACT

Compounds of formula (I):

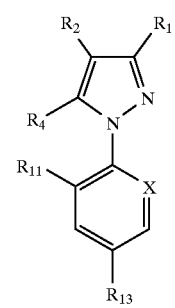

compositions containing them and methods of use to control pests.

22 Claims, No Drawings

PESTICIDAL 1-ARYLPYRAZOLE-5-SULFINILIMINE DERIVATIVES

CROSS-REFERENCE TO RELATED APPLICATION

This application claims the priority of U.S. Provisional patent application Ser. No. 60/030,019, filed Nov. 1, 1996, incorporated by reference herein in its entirety and relied upon.

The present invention relates to new 1-arylpyrazoles and derivatives thereof. The invention further pertains to compositions of said compounds and methods, use of said compounds for the control of pests, in particular to the application of said compounds or compositions in agricultural methods of use, particularly as pesticides, for controlling arthropods, especially insects by systemic action.

International Patent Publication No. WO 87/03781 and European Patent Publication No. 0295117 describe insecticidal 1-(substituted phenyl) pyrazoles. International Patent Publications No. WO 93/06089 and WO 94/21606 also describe insecticidal 1-(4-$SF_5$ substituted phenyl) heterocycles which may be pyrroles as well as imidazoles or pyrazoles. The teaching of these patents is not substantially different from International Patent Publication No. WO 87/03781 or from European Patent Publication No. 0295117 as far as pyrazoles are concerned.

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, miticidal, foliar insecticidal, soil insecticidal, systemic, antifeeding or pesticidal activity via seed treatment.

A fourth object of the present invention is to provide compounds with substantially enhanced and more rapid activity, especially against insects and more particularly insects in their larval stages.

A fifth object of the present invention is to provide compounds with greatly improved (faster and greater) penetration into pest species when topically applied and to thus provide enhanced movement of the compounds to the pesticidal site(s) of action within the pest.

These and other objects of the invention are met in whole and in part by the present invention. They shall become readily apparent from the description of the present invention which follows.

This invention embraces novel chemical compounds having an insecticidal or miticidal activity, with an improved systemic activity over the closest compounds.

The present invention provides compounds of formula (I):

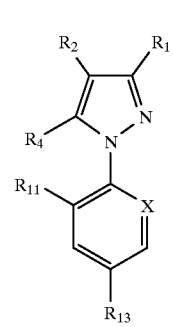

(I)

in which:

$R_1$ is CN or a halogen atom;

$R_2$ is $S(O)_nR_3$ or haloalkyl;

$R_3$ is alkyl or haloalkyl;

$R_4$ represents a $-N=SR_5R_6$ group;

$R_5$ and $R_6$ independently represent an alkyl, haloalkyl, alkoxyalkyl, acylalkyl or acyloxyalkyl radical; or $R_5$ and $R_6$ can together form a divalent alkylene radical which can be interrupted by one or two divalent heteroatoms, such as oxygen or sulfur;

$R_{11}$ and $R_{12}$ represent, independently of one another, a hydrogen or halogen atom, or CN or $NO_2$;

$R_{13}$ represents a halogen atom or a haloalkyl, haloalkoxy, $S(O)_qCF_3$ or $SF_5$ group;

X represents a trivalent nitrogen atom or a $C-R_{12}$ radical, the other three valences of the carbon atom forming part of the aromatic ring;

n and q represent, independently of one another, an integer equal to 0, 1, or 2;

or a pesticidally acceptable salt thereof;

with the proviso that when either $R_{11}$ or $R_{12}$ equal hydrogen, CN or $NO_2$ then the other must be halogen.

A preferred group of effective 1-arylpyrazoles of the present invention is that with one or more of the following features wherein:

$R_1$ is CN; $R_3$ is an alkyl radical; X is $C-R_{12}$;

$R_{11}$ and $R_{12}$ represent, independently of one another, a halogen atom; or $R_{13}$ is a haloalkyl radical.

A preferred group of compounds of formula (I) is that wherein:

$R_1$ is CN; $R_3$ is an alkyl radical; X is $C-R_{12}$;

$R_{11}$ and $R_{12}$ represent, independently of one another, a halogen atom; and $R_{13}$ is a haloalkyl radical.

In the instant invention, some words are used in a specific sense:

The term "lower alkyl-$S(O)_n$" means a radical of the formula $-S(O)_n-$ lower alkyl. The term "$R_{10}S(O)_n$" means a radical of the formula $-S(O)_nR_{10}$. Alkyl groups have generally 1 to 6 carbon atoms, preferably 1 to 4. The term "halo" before the name of a radical means that this radical is partially or completely halogenated, that is to say, substituted by F, Cl, Br, or I, in any combination, preferably by F or Cl. The term "halogen" means F, Cl, Br or I. The term "lower" before the name of a radical having a carbon skeleton means that this carbon skeleton has less than 6 carbon atoms. When the name of any substituent is repeated, it keeps the same meaning unless otherwise specified. The term "aryl" designates an aromatic radical which is preferably phenyl optionally substituted with one or more substituents selected from halogen, methyl and methoxy, especially phenyl, halophenyl, tolyl or xylyl. The term "acyl" designates an alkylcarbonyl radical. The various individual radicals (such as alkyl, alkenyl, alkynyl, alkoxy and alkylene or the like) contain up to six carbon atoms. The divalent alkylene radical formed by $R_5$ and $R_6$ and including the sulfur to which they are attached is generally a 5, 6, or 7-membered ring.

For the above preferred compounds, there are optimum combinations of substituent groups.

Preferred phenyl groups or pyridyl groups comprising the $R_{11}$–$R_{13}$ and X radicals in formula (I) are: 2,6-dichloro-4-trifluoromethylphenyl, 2,6-dichloro-4-trifluoromethoxyphenyl, 2-bromo-6-chloro-4-trifluoromethylphenyl, 2-bromo-6-chloro-4-trifluoromethoxyphenyl, 2,6-difluoro-4-trifluoromethylphenyl, 2-chloro-4-trifluoromethylphenyl, 3-chloro-5-trifluoromethyl- 2-pyridinyl, 3-chloro-5-trifluoromethoxy-2-pyridinyl, 3,5-dichloro-2-pyridinyl, 2,6-dichloro-4-bromophenyl, 2,4,6-trichlorophenyl, 2-bromo-6-fluoro-4-difluoromethylphenyl, 2-chloro-6-fluoro-4-trifluoromethylphenyl, 2,6-dibromo-4-trifluoromethylphenyl, 2,6-dibromo-4-trifluoromethoxyphenyl, or 2-bromo-4-trifluoromethylphenyl.

Further, preferred $S(O)_nR_3$ substituents in formula (I) are: methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

Particularly preferred pyrazole derivatives include the following, the numbers 1–5 being assigned to these compounds for reference and identification.

1) S,S-dimethyl-N-[3-cyano-4-ethylsulfinyl-1-{2,6-dichloro-4-(trifluoromethyl)phenyl}-5-(1H-pyrazolyl)] sulfilimine. Mp about 143° C.

2) S,S-dimethyl-N-[3-cyano-4-ethylthio-1-{2,6-dichloro-4-(trifluoromethyl)phenyl}-5-(1H-pyrazolyl)] sulfilimine. Mp about 148° C.

3) S,S-dimethyl-N-[3-cyano-4-ethylsulfonyl-1-{2,6-dichloro-4-(trifluoromethyl)phenyl}-5-(1H-pyrazolyl)] sulfilimine.

4) S,S-dimethyl-N-[3-cyano-4-methylthio-1-{2,6-dichloro-4-(trifluoromethyl)phenyl}-5-(1H-pyrazolyl)] sulfilimine. Mp about 170° C.

5) S,S-dimethyl-N-[3-cyano-4-methylsulfinyl-1-{2,6-dichloro-4-(trifluoromethyl)phenyl}-5-(1H-pyrazolyl)] sulfilimine.

Compound 1 is especially preferred.

Compounds of formula (I) may be prepared from compounds of formula (II)

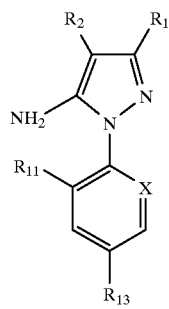

(II)

by reaction of a proper reactant introducing the =$SR_5R_6$ group.

Compounds of formula (II) are known. They are described, inter alia, in International Patent Publications n° WO 87/3781, 93/6089, and 94/21606 as well as in European Patent Applications 295117, 403300, 385809 or 679650. German Patent Publication 19511269 and U.S. Pat. Nos. 5,232,940 and 5,236,938 or other process according to the knowledge of a man skilled in the art of chemical synthesis, which is deemed to include the Chemical Abstract and the literature referred to therein.

According to a first method, a compound of formula (II) is reacted, preferably in a solvent, with a compound of formula $R_5$—S—$R_6$ in the presence of a halogenating agent and a base. The sulfides $R_5$—S—$R_6$ are those in which the substituents $R_5$ and $R_6$ are as defined above. Suitable bases include trialkylamines, such as triethylamine. As halogenating agents N-chlorosuccinimide, N-bromosuccinimide, chlorine or bromine may be employed; N-chlorosuccinimide (NCS) is preferred. Suitable solvents include hydrocarbons such as toluene and xylene; halogenated hydrocarbons such as dichloromethane, chloroform; ethers such as tetrahydrofuran, dioxane, diethyl ether. Reaction temperatures of about −70° C. to 50° C. may be employed; −30° C. to 0° C. is preferred.

According to a second method, a compound of formula (II) is reacted, preferably in a solvent, with a sulfoxide $R_5$—S(O)—$R_6$ in the presence of phosphoric anhydride and of a base. A typical sulfoxide is dimethyl sulfoxide; $R_5$ and $R_6$ are as defined above. Triethylamine or other trialkylamine is a suitable base. Appropriate solvents include hydrocarbons such as toluene and xylene; halogenated hydrocarbons such as dichloromethane, chloroform; ethers such as tetrahydrofuran, dioxane, diethyl ether. Reaction temperatures may range from about −50° C. to 60° C.

EXAMPLE 1

Preparation of Compound 1

A slurry of 3.0 g (0.00755 mol) of 5-amino-1-[2,6-dichloro-4-(trifluoromethyl)phenyl]-4-ethylsulfinyl-1H-pyrazole-3-carbonitrile in 110 mL of $CH_2Cl_2$ was stirred, with ice/water cooling, and treated, in succession, with 0.66 g (0.0106 mol) of dimethyl sulfide, 1.41 g (0.0106 mol) of N-chlorosuccinimide, added portion-wise over 30 min, and finally 2.88 g (0.0285 mol) of triethylamine, added dropwise. The mixture was stirred for about 17 hr at room temperature and then extracted with cold 5% NaOH and then with water. The organic layer was dried (MgSO$_4$), filtered and evaporated to give a residue. Chromatography on silica, eluting with 3:2 CH$_2$Cl$_2$/ethyl acetate gave 1.16 g (0.00254 mol) of the title compound.

Compound 2 is prepared by a similar method using the 5-amino-1-[2,6-dichloro-4-(trifluoromethyl)phenyl]-4-ethylthio-1H-pyrazole-3-carbonitrile as starting reagent.

Compound 4 can be prepared by a similar method using the 5-amino-1-[2,6-dichloro-4-(trifluoromethyl)phenyl]-4-methylthio-1H-pyrazole-3-carbonitrile as starting reagent. Its melting point is 170° C. This compound is hereinafter referred to as Compound No. 4.

EXAMPLE 2

Preparation of Compound 3

To a stirred solution of 1.20 gram (0.0035 mole) of 50% by weight 3-chloroperbenzoic acid in 35 mL of dichloromethane was added, dropwise, a solution of 0.94 gram (0.00205 mole) of S,S dimethyl-N-[3-cyano-4-ethylsulfinyl-1-{2,6-dichloro-4-(trifluoromethyl)phenyl}-5-(1H-pyrazolyl)]sulfilimine (Compound No. 1 prepared in Example 1) while stirring at 0–5° C. in an ice/water bath. The mixture was stirred for a 1.4 hour period, 0.25 mL of dimethyl sulfide added and the resulting mixture stored at 5° C. for an approximate 17-hour period. The reaction solution was extracted with saturated aqueous Na$_2$CO$_3$, back-extracting the aqueous layer with dichloromethane. The combined organic layers were water-washed, dried over MgSO$_4$ and evaporated to give an oil which was chromatographed on a silica column to give 0.34 gram (0.00071 mole) of the title compound having a molecular weight as determined by mass spectrometry of 472.

EXAMPLE 3

Preparation of Compound 5

Employing a procedure similar to that described in the above Example 1 a 10.0-gram (0.0261 mole) portion of 5-amino-1-[2,6-dichloro-4-(trifluoromethyl)phenyl]-4-methylsulfinyl-1H-pyrazole-3-carbonitrile was reacted with dimethylsulfide, N-chlorosuccinimide and triethylamine to give 6.4 grams (0.014 mole) of S,S-Dimethyl-N-[3-cyano-4-methylsulfinyl-1-{2,6-dichloro-4-(trifluoromethyl)phenyl}-5-(1H-pyrazolyl)]sulfilimine, 94.6 area % purity by HPLC, and having a molecular weight as determined by mass spectrometry of 442.

The present invention provides a method for controlling pests at a locus comprising applying to said locus a pesticidally, preferably arthropocidally, effective amount of a compound of formula (I), or a pesticidal preferably arthropocidal, composition comprising a pesticidally preferably arthropocidally, effective amount of a compound of formula (I) and a pesticidally acceptable carrier therefor (or an inert carrier which is acceptable in animal health). In a preferred embodiment, the invention provides a method for controlling insects at a locus comprising applying to said locus an insecticidally effective amount of a compound of formula (I), or an insecticidally effective amount of an insecticidal composition comprising an insecticidally effective amount of a compound of formula (I) and an agriculturally acceptable (or acceptable in animal health) inert carrier therefor. Preferably, the locus to which the arthropodicidally (especially insecticidally) effective amount is applied is a crop-growing area, that is, an area in which a crop is growing or in which a crop has been planted, or an area in which a crop will be planted/grown.

The compositions which can be used in the invention for the pesticidal/insecticidal treatment of the invention can comprise from about 0.001 to 95% of the active ingredient of formula (I).

The diluted liquid formulations, as applied to the locus to be treated or crop, generally comprise from about 0.001 to about 3% of active ingredient of formula (I), preferably from about 0.1 to about 0.5%.

The solid formulations as applied to the locus or crop generally comprise from about 0.1 to about 8% of active ingredient of formula (I), preferably from about 0.5 to about 1.5%.

The concentrated compositions are the compositions which are commercialized or transported or stored. For application to plants, they are normally diluted in water and applied in such diluted form. The diluted forms are part of the invention as well as the concentrated forms.

The concentrated formulations generally comprise from about 5 to about 95% of active ingredient of formula (I), preferably from about 10 to about 50%.

The insecticidal compositions of the invention can be applied once, or more than once, throughout the whole insect season. Insecticidal compositions according to the invention are usually applied to the locus to be treated or crop area at a rate of from about 0.01 to about 2 kg/ha of active ingredient, preferably from about 0.04 to about 2 kg/ha, most preferably from about 0.1 to about 1 kg/ha. The insecticidal compositions of the invention may be used also for seed treatment at a rate of from about 0.03 to about 40 g ai/kg of seed, preferably from about 0.1 to about 10 g ai/kg of seed.

The compounds of the invention are advantageously applied to plants or soil or seeds. It may be a foliar application or a soil application, such an application being made to control the pests located in other parts of the plant, that is to say in parts of the plant which are different from the part where the active material is applied. The soil application may be used to control soil insects before they feed in the plants or as they feed in the plants.

The concentrated insecticidal compositions according to the invention can be in the form of a solid, e.g. dusts or granules or wettable powders, or, preferably, in the form of a liquid, such as an emulsifiable concentrate or a true solution.

The compositions according to the instant invention generally comprise from about 0.5 to about 95% of active ingredient of formula (I). The remainder of the composition up to 100% comprises a carrier as well as various additives such as those hereafter indicated.

By "carrier", there is meant herein an organic or inorganic material, which can be natural or synthetic, and which is associated with the active ingredient and which facilitates its application to the locus to be treated or crop. This carrier is thus generally inert and should be agriculturally acceptable, especially on the contemplated or treated locus or crop. The carrier can be solid (clay, silicates, silica, resins, wax, fertilizers, etc.) or liquid (water, alcohols, ketones, oil solvents, saturated or unsaturated hydrocarbons, chlorinated hydrocarbons, liquified petroleum gas, etc.).

Among the many additives, the compositions of the invention can comprise surfactants as well as other ingredients such as dispersants, stickers, antifoam agents, antifreezing agents, dyestuffs, thickeners, adhesives, protective colloids, penetrating agents, stabilizing agents, sequestering agents, antiflocculating agents, corrosion inhibitors, pigments and polymers.

More generally, the compositions of the invention can comprise all kinds of solid or liquid additives which are known in the art of insecticides and insecticidal treatments.

The surfactants can be of the emulsifying or wetting type, ionic or nonionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives, such as alkyl taurates; phosphoric esters; or esters of alcohols or polyoxyethylated phenols. When the spraying vehicle is water, the use of at least one surfactant is generally required because the active ingredients are not water-soluble.

The method of application of the compositions of the invention is generally the spraying of a mixture which has been previously made, by dilution of more concentrated formulations according to the invention.

Solid compositions can be powders for dusting or for dispersion (wherein the content of active ingredient can be up to 100%) and granules, especially extruded or compacted granules, or granules which have been made by impregnation of a powder (the content of active ingredient in such powders being between about 1 and about 80%).

Liquid compositions or compositions which have to be liquid when applied include solutions, water-soluble concentrates, emulsifiable concentrates, emulsions, wettable powders or pastes or water-dispersible granules.

Emulsifiable concentrates generally comprise from about 10 to about 80% of active ingredient; the emulsions when applied generally comprise from about 0.01 to about 20% of active ingredient.

For example, the emulsifiable concentrates can comprise the solvent and, to the extent needed, from about 2 to about 20% of suitable additives such as stabilizers, surfactants, penetrating agents, corrosion inhibitors or other additives already recited.

These concentrates are usually diluted in tank water so as to obtain the dilution appropriate for spraying.

The concentrated suspensions can also be applied by spraying and have to be fluid without allowing any solid to separate and fall to the bottom. Generally they comprise from about 1 to about 75% of active ingredient (preferably from about 2 to about 50%), from about 0.5 to about 15% of surfactant, from about 0.1 to about 10% of thickener, from 0 to about 10% of other suitable additives as already indicated, the remainder being water or an organic liquid wherein the active ingredient is insoluble or has a low solubility.

The wettable powders generally comprise the active ingredient (from about 1 to about 95%, preferably from about 2 to about 80%), the solid carrier, a wetting agent (from 0 to about 5%), a dispersing agent (from about 3 to about 10%) and, to the extent needed, from 0 to about 10% of other additives such as stabilizers and others as already listed.

In order to obtain these wettable powders or dusting powders, it is appropriate to intimately mix the active ingredients and the additives, as by grinding in a mill or similar device.

Dispersible granules are generally made by agglomeration of a powder, followed by an appropriate granulation process.

The emulsions herein described can be of the oil-in-water or water-in-oil types. Fluidity of the emulsions can range from low viscosities up to high viscosities approaching those of gels.

Among these many compositions or formulations, one skilled in the art can choose the one most appropriate, according to the specific conditions of the treatment problem.

The compounds and compositions of the invention can also be used in admixtures with another pesticide, e.g., an insecticide, acaricide or herbicide.

The compounds of the invention may also be used in controlling pests found in non-agricultural domains.

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boophilus spp. e.g. *Boophilus microplus,* Amblyomma spp., Hyalomma spp., Rhipicephalus spp. e.g. *Rhipicephalus appendiculatus,* Haemaphysalis spp., Dermacentor spp., Ornithodorus spp. (e.g. *Ornithodorus moubata*) and mites (e.g. Damalinia spp., *Dermahyssus gallinae,* Sarcoptes spp. e.g. *Sarcoptes scabiei,* Psoroptes spp., Chorioptes spp;, Demodex spp., Eutrombicula spp.,); Diptera (e.g. Aedes spp., Anopheles spp., Dermatobia spp., Haematobia spp., Musca spp., Hippoboscidae spp., Hypoderma spp., Gasterophilus spp., Simulium spp); Stomoxys spp., Hemiptera (e.g. Triatoma spp); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei,* Cooperia spp. and *Hymenolepis nana;* in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoms cruzi,* Leishaminia spp., Plasmodium spp., Babesis spp., Trichomonadidae spp., Histomanas spp., Giardia spp., Toxoplasma spp., *Entamoeba histolytica* and Theileria spp.

Furthermore the compounds of the invention may be useful for coccidiosis, a disease caused by infections from protozoan parasites of the genus Eimeria.

Solid or liquid compositions for application topically to animals, timber, stored products or household goods usually contain from about 0.00005% to about 90%, more particularly from about 0.001% to about 10%, by weight of one or more compounds of general formula (I). For administration to animals orally or parenterally, including percutaneously solid or liquid compositions, these normally contain from about 0.1% to about 90% by weight of one or more compounds of general formula (I). Medicated feedstuffs normally contain from about 0.001% to about 3% by weight of one or more compounds of general formula (I). Concentrates or supplements for mixing with feedstuffs normally contain from about 5% to about 90%, preferably from about 5% to about 50%, by weight of one or more compounds of general formula (I). Mineral salt licks normally contain from about 0.1% to about 10% by weight of one or more compounds of general formula (I).

Dusts or liquid compositions for application to livestock, persons, goods, premises or outdoor areas may contain from about 0.0001% to about 15%, more especially from about 0.005% to about 2.0%, by weight, of one or more compounds of general formula (I). Suitable concentrations in treated waters are between about 0.0001 ppm and about 20 ppm, more particularly about 0.001 ppm to about 5.0 ppm of one or more compounds of general formula (I) and may be used therapeutically in fish farming with appropriate exposure times. Edible baits may contain from about 0.01% to about 5%, preferably from about 0.01% to about 1.0%, by weight, of one or more compounds of general formula (I).

When administered to vertebrates parenterally, orally or by percutaneous or other means, the dosage of compounds of general formula (I) will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following methods were used to apply the compounds of the invention and to observe the results obtained therewith: a foliar/contact spray on sucking (aphids) or chewing (Lepidoptera) insects.

| GENUS, SPECIES | COMMON NAME |
|---|---|
| *Aphis gossypii* | cotton leaf aphid |
| *Musca domestica* | housefly |

The Housefly Bait/Contact Application Method (*Musca domestica*)

About 25 four to six-day-old adult houseflies were anesthetized and placed in a cage with a sugar water bait solution containing the compound. The concentration of the selected compound of formula (I) in the bait solution was 100 ppm. After 24 hours, flies which showed no movement on stimulation were considered dead.

Foliar/Contact Application Method with *A. gossypii*

Aphid-infested cotton plants were placed on a revolving turntable, and sprayed to runoff with a 100 ppm formulation of the selected compound of formula (I). The treated, *A. gossypii*-infested plants were held for three days after treatment, after which the dead aphids were counted.

Compounds 1, 2, 3, 4 and 5 were found to be very active on both these application methods.

While the invention has been described in terms of various preferred embodiments, the person skilled in the art will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of formula (I):

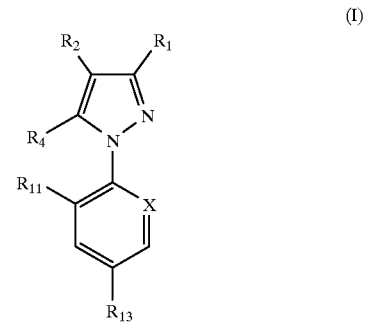

in which:

$R_1$ is CN or a halogen atom;

$R_2$ is $S(O)_n R_3$ or haloalkyl;

$R_3$ is alkyl or haloalkyl;

$R_4$ represents a $-N=SR_5R_6$ group;

$R_5$ and $R_6$ independently represent an alkyl, haloalkyl, alkoxyalkyl, acylalkyl or acyloxyalkyl radical; or $R_5$ and $R_6$ together form a divalent alkylene radical which is optionally interrupted by one or two divalent heteroatoms;

$R_{11}$ and $R_{12}$ represent, independently of each other, a hydrogen or halogen atom, or CN or $NO_2$;

$R_{13}$ represents a halogen atom or a haloalkyl, haloalkoxy, $S(O)_q CF_3$ or $SF_5$ group;

X represents a trivalent nitrogen atom or a $C-R_{12}$ radical, the other three valences of the carbon atom forming part of the aromatic ring;

n and q represent, independently of each other, an integer equal to 0, 1, or 2;

or a pesticidally acceptable salt thereof;

with the proviso that when one of $R_{11}$ and $R_{12}$ is hydrogen, CN or $NO_2$, then the other of them must be halogen.

2. A compound according to claim 1, having at least one feature selected from the group consisting of:

$R_1$ is CN;

$R_3$ is an alkyl radical;

X is $C-R_{12}$;

$R_{11}$ and $R_{12}$ represent, independently of each other, a halogen atom; and $R_{13}$ is a haloalkyl radical.

3. A compound according to claim 2, wherein:

$R_1$ is CN;

$R_3$ is an alkyl radical;

X is $C-R_{12}$;

$R_{11}$ and $R_{12}$ represent, independently of each other, a halogen atom; and $R_{13}$ is a haloalkyl radical.

4. A compound according to claim 1, wherein the ring system comprising the $R_{11}$–$R_{13}$ and X radicals in formula (I) is 2,6-dichloro-4-trifluoromethylphenyl, 2,6-dichloro-4-trifluoromethoxyphenyl, 2-bromo-6-chloro-4-trifluoromethylphenyl, 2-bromo-6-chloro-4-trifluoromethoxyphenyl, 2,6-difluoro-4-trifluoromethylphenyl, 2-chloro-4-trifluoromethylphenyl, 3-chloro-5-trifluoromethyl-2-pyridinyl, 3-chloro-5- trifluoromethoxy-2-pyridinyl, 3,5-dichloro-2-pyridinyl, 2,6-dichloro-4-bromophenyl, 2,4,6-trichlorophenyl, 2-bromo-6-fluoro-4-difluoromethylphenyl, 2-chloro-6-fluoro-4-trifluoromethylphenyl, 2,6-dibromo-4-trifluoromethylphenyl, 2,6-dibromo-4-trifluoromethoxyphenyl, or 2-bromo-4-trifluoromethylphenyl.

5. A compound according to claim 2, wherein the ring system comprising the $R_{11}$–$R_{13}$ and X radicals in formula (I) is 2,6-dichloro-4-trifluoromethylphenyl, 2,6-dichloro-4-trifluoromethoxyphenyl, 2-bromo-6-chloro-4-trifluoromethylphenyl, 2-bromo-6-chloro-4-trifluoromethoxyphenyl, 2,6-difluoro-4-trifluoromethylphenyl, 2-chloro-4-trifluoromethylphenyl, 3-chloro-5-trifluoromethyl-2-pyridinyl, 3-chloro-5-trifluoromethoxy-2-pyridinyl, 3,5-dichloro-2-pyridinyl, 2,6-dichloro-4-bromophenyl, 2,4,6-trichlorophenyl, 2-bromo-6-fluoro-4-difluoromethylphenyl, 2-chloro-6-fluoro-4-trifluoromethylphenyl, 2,6-dibromo-4-trifluoromethylphenyl, 2,6-dibromo-4-trifluoromethoxyphenyl, or 2-bromo-4-trifluoromethylphenyl.

6. A compound according to claim 3, wherein the ring system comprising the $R_{11}$–$R_{13}$ and X radicals in formula (I) is 2,6-dichloro-4-trifluoromethylphenyl, 2,6-dichloro-4-trifluoromethoxyphenyl, 2-bromo-6-chloro-4-trifluoromethylphenyl, 2-bromo-6-chloro-4-trifluoromethoxyphenyl, 2,6-difluoro-4-trifluoromethylphenyl, 2-chloro-4-trifluoromethylphenyl, 3-chloro-5-trifluoromethyl-2-pyridinyl, 3-chloro-5-trifluoromethoxy-2-pyridinyl, 3,5-dichloro-2-pyridinyl, 2,6-dichloro-4-bromophenyl, 2,4,6-trichlorophenyl, 2-bromo-6-fluoro-4-difluoromethylphenyl, 2-chloro-6-fluoro-4-trifluoromethylphenyl, 2,6-dibromo-4-trifluoromethylphenyl, 2,6-dibromo-4-trifluoromethoxyphenyl, or 2-bromo-4-trifluoromethylphenyl.

7. A compound according to claim 1, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

8. A compound according to claim 2, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

9. A compound according to claim 3, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

10. A compound according to claim 4, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

11. A compound according to claim 5, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

12. A compound according to claim 6, wherein the $S(O)_nR_3$ substituent in formula (I) is methylthio, methylsulfinyl, methylsulfonyl, ethylsulfinyl, ethylsulfonyl, ethylthio, cyclopropylsulfinyl, cyclopropylthio, cyclopropylsulfonyl, isopropylsulfinyl, isopropylsulfonyl, or isopropylthio.

13. The compound according to claim 1, which is:

S,S-dimethyl-N-[3-cyano-4-ethylsulfinyl-1-{2,6-dichloro-4-(trifluoromethyl)phenyl}-5-(1H-pyrazolyl)]sulfilimine;

S,S-dimethyl-N-[3-cyano-4-ethylthio-1-{2,6-dichloro-4-(trifluoromethyl)phenyl}-5-(1H-pyrazolyl)]sulfilimine;

S,S-dimethyl-N-[3-cyano-4-ethylsulfonyl-1-{2,6-dichloro-4-(trifluoromethyl)phenyl}-5-(1H-pyrazolyl)]sulfilimine;

S,S-dimethyl-N-[3-cyano-4-methylthio-1-{2,6-dichloro-4-(trifluoromethyl)phenyl}-5-(1H-pyrazolyl)]sulfilimine; or S,S-dimethyl-N-[3-cyano-4-methylsulfinyl-1-{2,6-dichloro-4-(trifluoromethyl)phenyl}-5-(1H-pyrazolyl)]sulfilimine.

14. A pesticidal composition comprising:
(a) a pesticidally effective amount of a compound of formula (I):

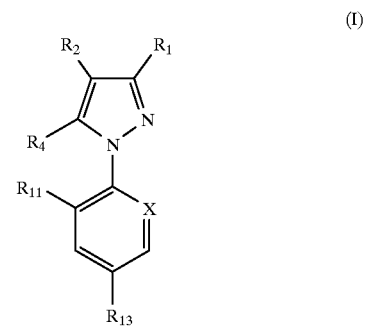

in which:

$R_1$ is CN or a halogen atom;

$R_2$ is $S(O)_nR_3$ or haloalkyl;

$R_3$ is alkyl or haloalkyl;

$R_4$ represents a —N=SR$_5$R$_6$ group;

$R_5$ and $R_6$ independently represent an alkyl, haloalkyl, alkoxyalkyl, acylalkyl or acyloxyalkyl radical; or $R_5$ and $R_6$ together form a divalent alkylene radical which is optionally interrupted by one or two divalent heteroatoms;

$R_{11}$ and $R_{12}$ represent, independently of each other, a hydrogen or halogen atom, or CN or $NO_2$;

$R_{13}$ represents a halogen atom or a haloalkyl, haloalkoxy, $S(O)_qCF_3$ or $SF_5$ group;

X represents a trivalent nitrogen atom or a C—$R_{12}$ radical, the other three valences of the carbon atom forming part of the aromatic ring;

n and q represent, independently of each other, an integer equal to 0, 1, or 2;

or a pesticidally acceptable salt thereof;

with the proviso that when one of $R_{11}$ and $R_{12}$ is hydrogen, CN or $NO_2$, then the other of them must be halogen; and (b) a pesticidally acceptable carrier therefor.

15. A composition according to claim 14, comprising from 0.001 to 95% of compound of formula (I).

16. A method for controlling pests at a locus comprising applying to said locus a pesticidally effective amount of a compound of formula (I):

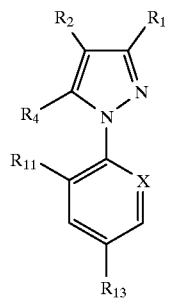

(I)

in which:

R₁ is CN or a halogen atom;

R₂ is $S(O)_nR_3$ or haloalkyl;

R₃ is alkyl or haloalkyl;

R₄ represents a —N=SR₅R₆ group;

R₅ and R₆ independently represent an alkyl, haloalkyl, alkoxyalkyl, acylalkyl or acyloxyalkyl radical; or R₅ and R₆ together form a divalent alkylene radical which is optionally interrupted by one or two divalent heteroatoms;

R₁₁ and R₁₂ represent, independently of each other, a hydrogen or halogen atom, or CN or NO₂;

R₁₃ represents a halogen atom or a haloalkyl, haloalkoxy, $S(O)_qCF_3$ or SF₅ group;

X represents a trivalent nitrogen atom or a C—R₁₂ radical, the other three valences of the carbon atom forming part of the aromatic ring;

n and q represent, independently of each other, an integer equal to 0, 1, or 2;

or a pesticidally acceptable salt thereof;

with the proviso that when one of R₁₁ and R₁₂ is hydrogen, CN or NO₂, then the other of them must be halogen.

17. A method according to claim 16, wherein said pests are insects and wherein said pesticidally effective amount is an insecticidally effective amount.

18. A method according to claim 17, comprising applying to said locus from about 0.01 to about 2 kg/ha of compound of formula (I).

19. A method according to claim 18, comprising applying to said locus from about 0.1 to about 1 kg/ha of compound of formula (I).

20. A method for controlling pests at a locus comprising applying to said locus a pesticidally-effective amount of a composition comprising:

(a) a pesticidally effective amount of a compound of formula (I):

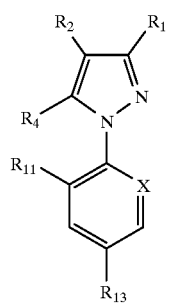

(I)

in which:

R₁ is CN or a halogen atom;

R₂ is $S(O)_nR_3$ or haloalkyl;

R₃ is alkyl or haloalkyl;

R₄ represents a —N=SR₅R₆ group;

R₅ and R₆ independently represent an alkyl, haloalkyl, alkoxyalkyl, acylalkyl or acyloxyalkyl radical; or R₅ and R₆ together form a divalent alkylene radical which is optionally interrupted by one or two divalent heteroatoms;

R₁₁ and R₁₂ represent, independently of each other, a hydrogen or halogen atom, or CN or NO₂;

R₁₃ represents a halogen atom or a haloalkyl, haloalkoxy, $S(O)_qCF_3$ or SF₅ group;

X represents a trivalent nitrogen atom or a C—R₁₂ radical, the other three valences of the carbon atom forming part of the aromatic ring;

n and q represent, independently of each other, an integer equal to 0, 1, or 2;

or a pesticidally acceptable salt thereof;

with the proviso that when one of R₁₁ and R₁₂ is hydrogen, CN or NO₂, then the other of them must be halogen; and (b) a pesticidally acceptable carrier therefor.

21. A method according to claim 20, wherein said pests are insects and wherein said pesticidally effective amount is an insecticidally effective amount.

22. A process for preparing a compound of formula (I) according to claim 1, which comprises:

(a) reacting a compound of formula (II):

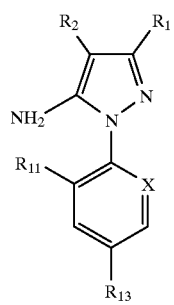

(II)

wherein $R_1$, $R_2$, $R_{11}$, $R_{13}$, and X are as defined in claim 1 with a compound of the formula $R_5$—S—$R_6$ wherein $R_5$ and $R_6$ are as defined in claim 1, in the presence of a halogenating agent and a base; or (b) reacting a compound of formula (II) above with a sulfoxide of the formula $R_5$—S(O)—$R_6$ wherein $R_5$ and $R_6$ are as defined in claim 1, in the presence of phosphoric anhydride and a base.

* * * * *